(12) United States Patent
Robbins et al.

(10) Patent No.: US 7,108,698 B2
(45) Date of Patent: Sep. 19, 2006

(54) COMBINED DISTRACTOR AND RETRACTOR INSTRUMENT AND METHODS

(75) Inventors: Daniel S. Robbins, North Bennington, VT (US); Erik E. Emstad, St. Paul, MN (US)

(73) Assignee: Zimmer Spine, Inc., Minneapolis, MN (US)

( * ) Notice: Subject to any disclaimer, the term of this patent is extended or adjusted under 35 U.S.C. 154(b) by 198 days.

(21) Appl. No.: 10/756,040

(22) Filed: Jan. 13, 2004

(65) Prior Publication Data

US 2005/0154395 A1 Jul. 14, 2005

(51) Int. Cl.
*A61B 17/60* (2006.01)

(52) U.S. Cl. .................. 606/90; 606/86; 606/105; 600/210

(58) Field of Classification Search ............. 600/210, 600/226, 217, 86, 220, 235, 237, 239, 240, 600/242, 243, 201, 211; 606/86, 90, 105, 606/53; 623/17.11–17.16
See application file for complete search history.

(56) References Cited

U.S. PATENT DOCUMENTS

| | | | | |
|---|---|---|---|---|
| 4,232,660 A * | 11/1980 | Coles | ................... | 600/210 |
| 4,347,845 A * | 9/1982 | Mayfield | ................ | 606/86 |
| 5,217,463 A | 6/1993 | Mikhail | | |
| 5,431,658 A * | 7/1995 | Moskovich | ............ | 606/99 |
| 5,624,446 A * | 4/1997 | Harryman, II | .......... | 606/96 |
| 5,776,199 A * | 7/1998 | Michelson | ............ | 623/17.16 |
| 5,885,300 A | 3/1999 | Tokuhashi et al. | | |
| 6,039,761 A * | 3/2000 | Li et al. | ............... | 623/17.16 |
| 6,042,538 A * | 3/2000 | Puskas | ................ | 600/114 |
| 6,083,225 A * | 7/2000 | Winslow et al. | ......... | 606/61 |
| 6,159,215 A * | 12/2000 | Urbahns et al. | .......... | 606/86 |
| 6,190,414 B1 * | 2/2001 | Young et al. | ........... | 623/17.15 |
| 6,193,653 B1 * | 2/2001 | Evans et al. | ............ | 600/210 |
| 6,200,322 B1 | 3/2001 | Branch et al. | | |
| 6,325,827 B1 * | 12/2001 | Lin | ................ | 623/17.16 |
| 6,500,206 B1 * | 12/2002 | Bryan | ................ | 623/17.16 |
| 6,506,151 B1 | 1/2003 | Estes et al. | | |
| 6,565,574 B1 * | 5/2003 | Michelson | ............ | 606/90 |
| 6,599,294 B1 * | 7/2003 | Fuss et al. | ............. | 606/99 |
| 6,663,637 B1 * | 12/2003 | Dixon et al. | ........... | 606/90 |
| 6,855,148 B1 * | 2/2005 | Foley et al. | ............ | 606/86 |
| 6,855,149 B1 * | 2/2005 | Dye | ................ | 606/90 |
| 2002/0013514 A1 * | 1/2002 | Brau | ................ | 600/213 |
| 2002/0026191 A1 | 2/2002 | Dixon et al. | | |
| 2002/0049368 A1 * | 4/2002 | Ritland | ............... | 600/210 |
| 2002/0165550 A1 | 11/2002 | Frey et al. | | |
| 2003/0032966 A1 | 2/2003 | Foley et al. | | |
| 2003/0139814 A1 * | 7/2003 | Bryan | ................ | 623/17.11 |
| 2003/0158557 A1 * | 8/2003 | Cragg et al. | ........... | 606/86 |
| 2003/0220689 A1 * | 11/2003 | Ritland et al. | .......... | 623/16.11 |
| 2003/0236447 A1 * | 12/2003 | Ritland | ............... | 600/210 |
| 2004/0162616 A1 * | 8/2004 | Simonton et al. | ........ | 623/17.11 |
| 2005/0113838 A1 * | 5/2005 | Phillips et al. | ........... | 606/80 |

* cited by examiner

FOREIGN PATENT DOCUMENTS

WO WO/0003654 1/2000

*Primary Examiner*—Patricia Bianco
*Assistant Examiner*—Patrick J. Kilkenny
(74) *Attorney, Agent, or Firm*—Wood, Herron & Evans, LLP

(57) ABSTRACT

A surgical instrument for use during a spinal surgery procedure. The surgical instrument being configured to distract two adjacent vertebral elements and retract the nerve root to provide access to the distracted site. The instrument including an elongated blade member having a wing located on an edge of the blade member, and a handle.

11 Claims, 4 Drawing Sheets

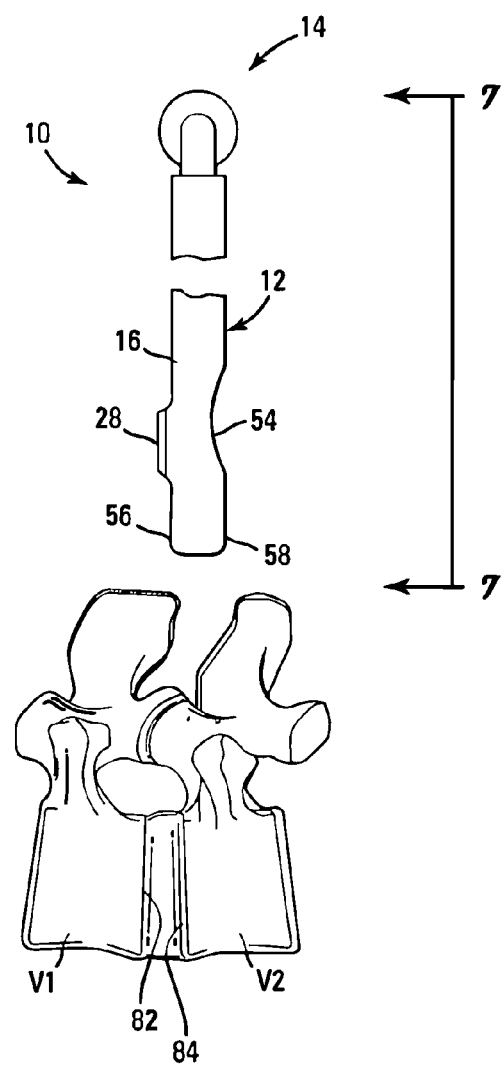
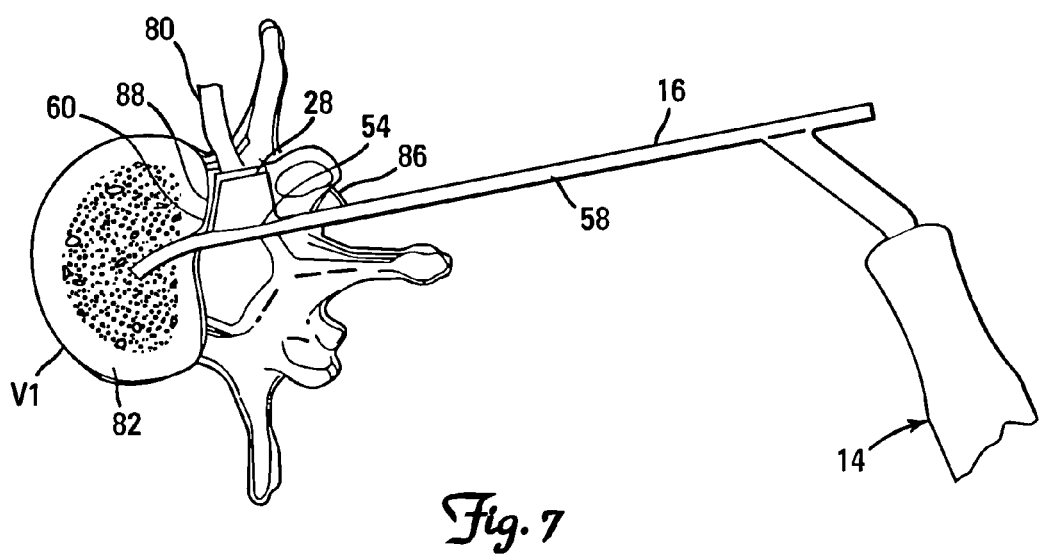

COMBINED DISTRACTOR AND RETRACTOR INSTRUMENT AND METHODS

TECHNICAL FIELD

This disclosure relates generally to methods and devices for accessing an area of a patient's spinal column during a surgical procedure. More particularly, this disclosure relates to an instrument that provides an accessible space between two vertebral elements.

BACKGROUND

A wide variety of surgical techniques have been used to access the spinal column in spinal surgery procedures. For example, some techniques include making an incision in the patient's back and retracting or separating tissue and muscle to expose a wide area of the spine in order to perform the spinal surgery procedure. The invasiveness of such techniques often results in excessive damage to the normal anatomy, and significant and dangerous blood loss.

In an attempt to minimize risks associated with spinal surgery procedures, some surgical techniques have been developed wherein only portions of the spinal column area are accessed during various stages of the surgical procedure. In these procedures, a smaller incision can be used to access a particular portion of the spinal column area. However, access to only a particular portion of the spinal column area does not provide sufficient access for all surgical procedures.

In general, improvement has been sought with respect to such surgical techniques, generally to better provide sufficient accessibility to a spinal column area while minimizing anatomical trauma and blood loss.

SUMMARY

One aspect of the present disclosure relates to a surgical instrument for distracting a space between adjacent vertebral elements and retracting the nerve root to provide access to the distracted space. The instrument includes an elongated member having a first end and a second end, the first end defining a curved region. The instrument also includes a handle extending from the elongated member and a wing extending outward from the elongated member. The handle is positioned adjacent to the second end of the elongated member and the wing is positioned adjacent to the first end of the elongated member.

Another aspect of the present disclosure relates to a surgical instrument having an elongated member having a longitudinal axis that extends from a first end to a second end. The elongated member has first and second edges that extend generally parallel to the longitudinal axis. The instrument further includes a handle positioned adjacent to the second end of the elongated member. A wing extends outward from one of the first and second edges of the elongated member and a recess is formed in the other of the first and second edges of the elongated member.

Still another aspect of the present disclosure relates to a distracting first and second adjacent vertebral elements. The method includes providing a surgical instrument having an elongated blade member, the elongated blade member having a longitudinal axis extending between a first end and a second end, and a wing located adjacent to the first end. The method further includes inserting the surgical instrument in a first orientation between the first and second vertebral elements and rotating the instrument to distract the first and second vertebral elements a distance.

A variety of examples of desirable product features or methods are set forth in part in the description that follows, and in part will be apparent from the description, or may be learned by practicing various aspects of the disclosure. The aspects of the disclosure may relate to individual features as well as combinations of features. It is to be understood that both the foregoing general description and the following detailed description are explanatory only, and are not restrictive of the claimed invention.

BRIEF DESCRIPTION OF THE DRAWINGS

FIG. 6 is a bottom plan view of the surgical instrument of FIG. 5, shown in a second relation to the first and second vertebral elements; and FIG. 7 is a view of the surgical instrument of FIG. 6, shown from a direction represented by line 7—7, and shown in the second relation to the vertebral elements (only the second vertebral element is illustrated).

DETAILED DESCRIPTION

Reference will now be made in detail to various features of the present disclosure that are illustrated in the accompanying drawings. Wherever possible, the same reference numbers will be used throughout the drawings to refer to the same or like parts.

Figure 1:
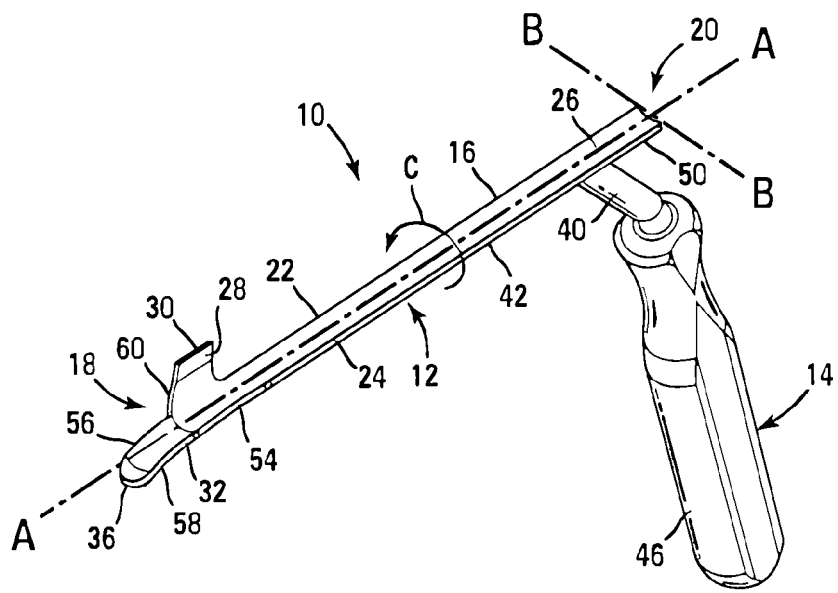
FIG. 1 is a perspective view of one embodiment of a surgical instrument according to the principals of the present disclosure, the embodiment having a left-handed configuration.

FIGS. 1–7 illustrate a surgical instrument embodiment having features that are examples of how inventive aspects in accordance with the principals of the present disclosure may be practiced. Referring to FIG. 1, the surgical instrument 10 includes an elongated member 12 and a handle 14. A surgeon, for example, grasps the handle 14 to manipulate the elongated member 12 during use. That is, the handle 14 is used to apply an insertion force and can be use to rotate the surgical instrument 10 to a desired orientation in relation to the vertebral elements during a surgical procedure. The handle 14 is also used to remove the elongated member 12 of the surgical instrument from between the vertebral elements.

Figure 2:
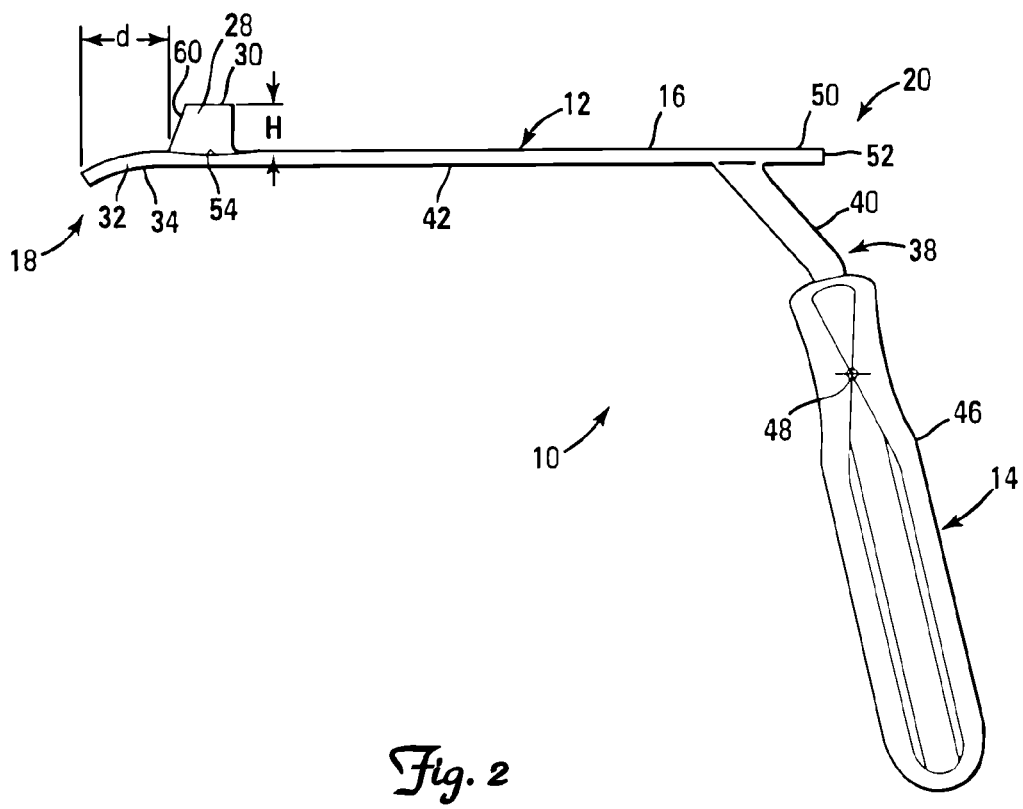
FIG. 2 is a first side elevational view of the surgical instrument of FIG. 1.

Referring now to FIGS. 1 and 2, the elongated member 12 generally defines a blade 16. The blade 16 has a first end 18 and a second end 20 that defines a longitudinal axis A—A of the elongated member 12. The blade has first and second edges 22, 24 extending generally parallel to the longitudinal axis. In the illustrated embodiment, the blade 16 has a concave curvature 26 relative to a plane BB (represented by line BB) defined by the first and second edges 22, 24. The concave curvature 26 is generally perpendicular to the longitudinal axis A—A of the blade 16 and typically extends along a majority of the blade 16. In the illustrated, the concave curvature extends from the first end 18 of the blade to the second end 20.

Still referring to FIGS. 1 and 2, a wing 28 is located adjacent to the first end 18 of the blade 16 along one of the first and second edges 22, 24 of the blade 16. In the illustrated embodiment of FIGS. 1 and 2, the wing 28 is located along the first edge 22 for use in a left-handed application. That is, the surgical instrument 10 having the wing 28 located on the first edge 22 is for use in an application wherein the two vertebral elements are accessed from a posterior approach, and from a patient-left side of the two vertebral elements.

Figure 3:
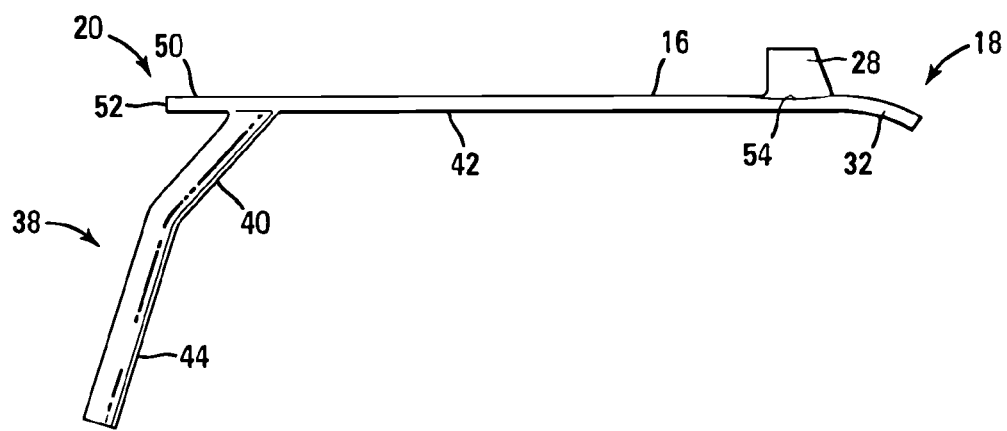
FIG. 3 is a second side elevational view of the surgical instrument, the embodiment having a right-handed configuration, and shown without a handle.
Figure 4:
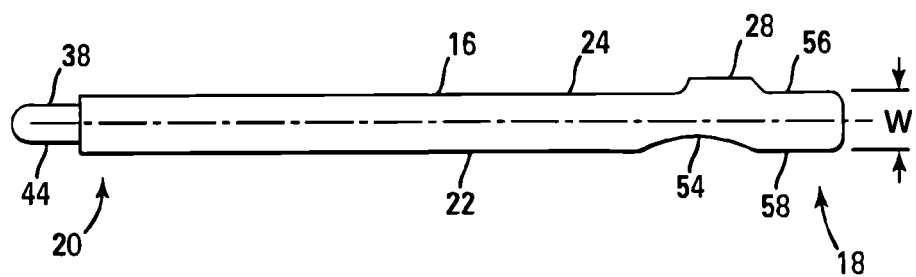
FIG. 4 is a top plan view of the surgical instrument of FIG. 3.

In the illustrated embodiment of FIGS. 3 and 4, the wing 28 is located along the second edge 24 for use in a right-handed application. That is, the surgical instrument 10 having the wing 28 located on the second edge 24 is for use in an application wherein the two vertebral elements are accessed from a posterior approach, and from a patient-right side of the two vertebral elements. During a surgical procedure, either the right-handed instrument or the left-handed instrument can be used when accessing the vertebral elements from the respective patient-right or patient-left side.

The wing 28 extends generally perpendicular to the plane BB defined by the first and second edges 22, 24 of the blade 16. Referring to FIG. 2, the wing 28 has a height H extending from a top edge 30 of the wing 28 to the plane BB (FIG. 1); although the disclosed principles can be applied in a variety of sizes and applications. The height H of the wing is preferably between 5 and 15 mm; more preferably between 8 and 12 mm.

In addition, the wing 28 is located a distance d from the first end 18 of the blade 16. The distance d extends from a rounded tip 36 (FIG. 1) at the first end 18 of the blade 16 to a front edge 60 of the wing 28. The distance d of the wing is preferably between 12 and 30 mm; more preferably between 18 and 26 mm.

Still referring to FIGS. 1 and 2, the blade 16 has a generally linear region 42 and a curved region 32. The curved region 32 is located at the first end 18 of the blade 16. The curved region 32 curves away from the plane BB defined by the first and second edges 22, 24 of the blade 16. That is, the curved region 32 has a convex curvature 34 that curves downward from the plane BB of the blade 16. The curved region 32 extends into the rounded tip 36 of the blade 16.

The handle 14 is located adjacent the second end 20 of the blade 16. The handle 14 includes a handle shaft 38 (FIG. 3) having an angled portion 40 and an extension portion 44. The angled portion 40 positions the extension portion 44 so that the surgical instrument 10 is easily and ergonomically maneuverable. A handle grip 46 is attached to the extension portion 44 of the handle shaft 38. The handle grip 46 can be attached by a fastener 48, such as a pin or threaded member, or may be attached by a bonding agent or weldment, for example.

Referring again to FIG. 1, a cutout section or recess 54 is located adjacent to the first end 18 of the blade 16 along one of the first and second edges 22, 24 of the blade 16. In particular, the recess 54 is located on the edge opposite the wing 28. In the left-handed embodiment of FIG. 1, the recess 54 is formed along the second edge 24 of the blade 16. In the right-handed embodiment of FIG. 4, the recess 54 is formed along the first edge 22 of the blade 16.

In the illustrated embodiment the recess 54 defines a curvature having a radius of approximately 1.5 inches. As will be described in greater detail hereinafter, the recess 54 provides clearance during use to permit the surgical tool 10 to be rotated or oriented from a first orientation relative to the vertebral elements to a second orientation.

Referring to FIGS. 2 and 3, the second end 20 of the blade 16 includes an extension 50 that extends outward from the blade 16 along the longitudinal axis A—A. The extension 50 defines an impact surface 52. The impact surface 52 can be defined only by the extension 50 of the blade 16, or may include a shaped surface or other structure designed to receive impact and positioned at the second end 20 of the surgical instrument.

Figure 5:
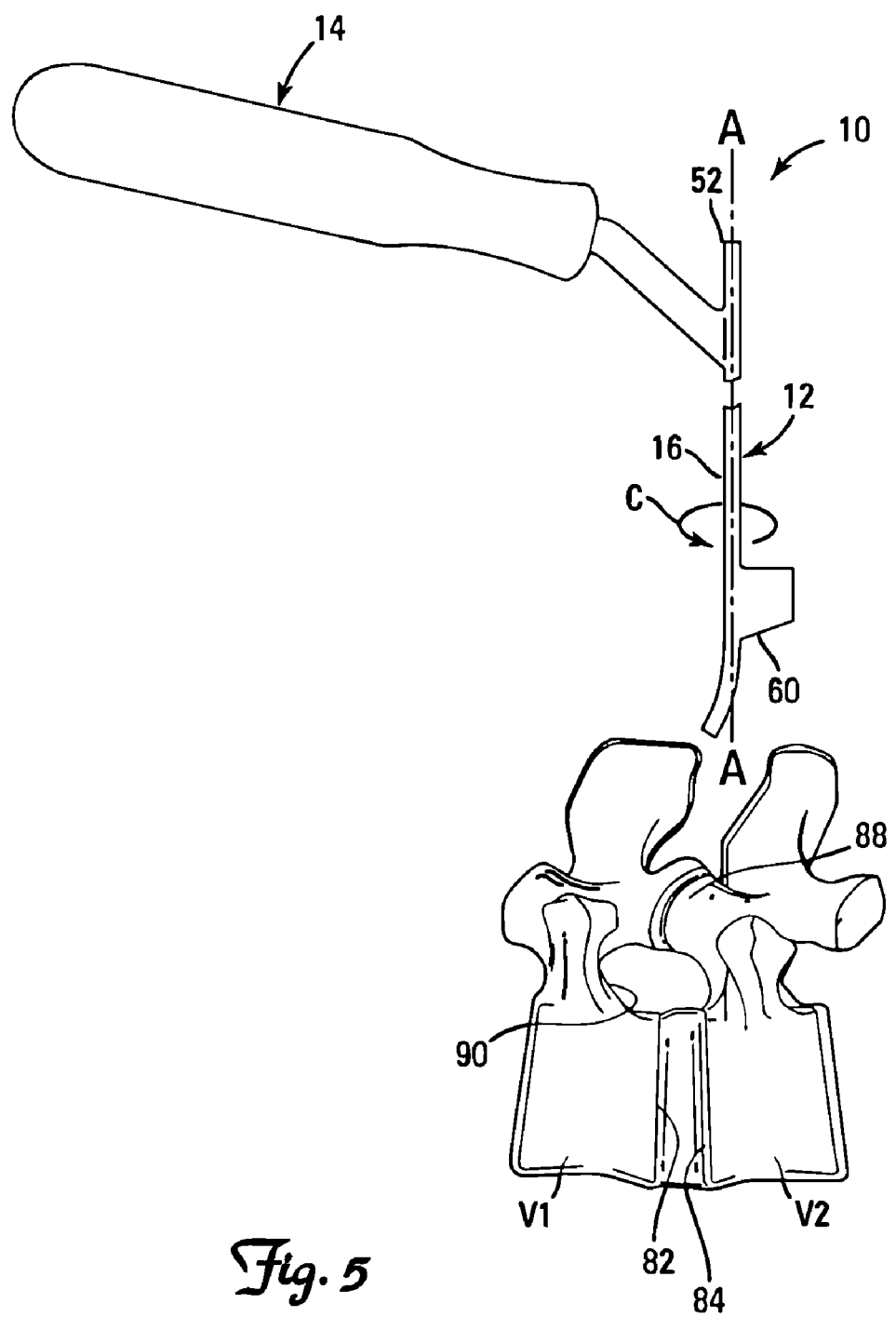
FIG. 5 is a side elevational view of the surgical instrument, having a left-handed configuration, shown in a first relation to first and second vertebral elements.

Referring now to FIGS. 5–7, in use, the surgical instrument 10 may be used to distract two adjacent vertebral elements V1, V2. Prior to use of the instrument 10, portions of the lamina 86 (FIG. 7) of the first vertebral element V1 and the inferior facet 88 (FIG. 5) of the second vertebral element V2 are typically removed to provide access to the distraction site. (E.g., a lateral aspect of the lamina of the first vertebral element V1 and a superior aspect of the inferior facet of the second vertebral element V2 are typically removed.) In this particular application shown, the instrument is a left-handed instrument and the procedure is being performed on the patient-left side of the two vertebral bodies.

To insert the instrument 10, the instrument is oriented such that the handle 14 is directed toward the head of a patient when the patient is lying on his front, as shown in FIG. 5. The instrument 10 is then inserted between the inferior endplate 82 of the first vertebral element V1 and the superior endplate 84 of the second vertebral element V2. The rounded tip 36 (FIG. 1) of the instrument 10 aids in insertion. The surgeon may also use a tap hammer (not shown) on the impact surface 52 of the blade 16 to assist in insertion of the instrument 10.

The distance d of the wing 28 from the first end 18 (FIG. 2) is configured to limit the insertion depth of the instrument 10. That is, the front edge 60 of the wing 28 functions as a stop. During use, the front edge 60 contacts the posterior aspect 88 of the first vertebral element V1 (FIG. 7) to indicate to the surgeon that the proper insertion depth of the instrument 10 has been reached.

To distract the first and second vertebral elements, the instrument 10 is rotated typically about 90 degrees in a direction C (FIG. 5) about the longitudinal axis A—A of the blade 16. Referring back to FIG. 1, the direction C is in the direction toward the wing 28. Thus, the direction C of rotation of the right-handed embodiment will be opposite the direction C of rotation of the left-handed embodiment.

FIG. 6 illustrates the orientation of the instrument 10 of FIG. 5 in relation to the vertebral elements when rotated 90 degrees to a distracted position. As the instrument 10 is rotated, the wing 28 sweeps around in an arc to retract the nerve root 80 (FIG. 7). The wing 28 gently holds the nerve root 80 located at the inferior aspect of the first vertebral element V1 in a stationary position. As shown in FIG. 7, when positioned in the distracted orientation, the wing 28 retracts or holds the nerve root out 80 of the way so that the surgeon can easily access the distracted site.

The recess 54 formed on one of the first and second edges 22, 24 of the blade 16 provides for clearance for the inferior aspect of a superior pedical 90 (FIG. 5) of the first vertebral element V1. That is, while the surgeon is rotating the instrument 10 from the first position shown in FIG. 5 to the second position shown in FIGS. 6 and 7, the recess 54 permits the blade 16 to rotate without interference. This reduces the amount of bone removal necessary to access the distraction site as required by conventional distraction procedures.

The curved region 32 of the surgical instrument 10 assists in protecting the dura (not shown) medially during and after insertion of the instrument. In addition, the curved region 32 provides stability when rotated to the second position or the distraction position shown in FIGS. 6 and 7. That is, support edges or surfaces 56, 58 of the curved region 32 (FIG. 1) contact the superior and inferior endplates of the vertebral elements in a non-linear fashion. This arrangement distributes the contact points of the support surface 56, 58 in a non-linear arrangement to increase the support stability as compared to an instrument having a straight edge or end.

As can be understood, the distance of distraction or the space created between the first and second vertebral elements V1, V2 is determined by a width W (FIG. 4) of the first end 18 of the blade 16. Referring back to FIG. 4, the width W of the first end 18 extends between the support surfaces 56, 58 of the blade 16. The width W is preferably between 5 and 15 mm; more preferably between 6 and 12 mm. Typically, the surgeon chooses a blade 16 having a particular width that corresponds to the size of the implant that is to be inserted between the first and second vertebral elements.

With the two vertebral elements V1, V2 distracted, and the nerve root 80 retracted by the instrument 10, the surgeon can insert tools to prepare the distracted site for insertion of a spinal implant. For example, boring tools can inserted into the distracted site to drill and ream the site for implantation. The concave curvature 26 of the blade 16 guides the boring tool to the distracted site. That is, the radius of the concave curvature 26 cradles diametrically configured tools to guide the tools axially along the longitudinal axis A—A of the surgical instrument 10. The concave curvature 26 can also be used to guide the implant and implant insertion tools.

The curved region 32 of the first end 18 of the blade further assists the surgeon during a surgical procedure by providing visual access to the distracted site. The curve region 32 curves away from the location where, for example, an implant bore is formed. The surgeon can look down the longitudinal axis A—A of the instrument 10 and better view the formed implant bore, as the first end of the instrument 10 at the distracted site curves away from the formed implant bore and the longitudinal axis A—A of the instrument 10.

In an alternative method of use, the surgical tool 10 may simple be inserted between the first and second vertebral elements in the distracted position as shown in FIG. 6. That is, the surgical instrument may be oriented as shown in FIG. 6, and inserted between the elements as shown. The rounded tip 36 of the instrument 10 aids in insertion as the first and second support surface 56, 58 contact the superior and inferior endplates 82, 84. Similar to the previous method, the surgeon may also use a tap hammer on the impact surface 52 of the blade 16 to assist in insertion.

The above specification provides a complete description of the COMBINED DISTRACTOR AND RETRACTOR INSTRUMENT. Since many embodiments of the invention can be made without departing from the spirit and scope of the invention, certain aspects of the invention reside in the claims hereinafter appended.

What is claimed is:

1. A surgical instrument, comprising:
    a) an elongated member having a first end and a second end, and a first edge and a second edge, the first end defining a curved region, wherein the curved region of the elongated member has a convex curvature relative to the plane defined by the first and second edges of the elongated member, the second edge further including a recess formed in the elongated member;
    b) a handle extending from the elongated member, the handle being positioned adjacent to the second end of the elongated member; and
    c) a wing extending outward from the first edge of the elongated member, the wing being positioned between the curved region and the handle; wherein the wing is used to retract a nerve root.

2. The instrument of claim 1, wherein the recess is formed adjacent to the first end of the elongated member.

3. The instrument of claim 2, wherein the curved region extends to a rounded tip.

4. The instrument of claim 3, wherein the first and second edges extend generally parallel to a longitudinal axis of the elongated member.

5. The instrument of claim 1, wherein the elongated member has a concave curvature relative to a plane defined by the first and second edges, the concave curvature extending along a majority of the elongated member.

6. A surgical instrument, comprising:
    a) an elongated member including a longitudinal axis extending from a first end to a second end, and first and second edges extending generally parallel to the longitudinal axis;
    b) a handle positioned adjacent to the second end of the elongated member;
    c) a wing extending outward from one of the first and second edges of the elongated member; and the wing being positioned between the first end and the handle
    d) a recess formed in the other of the first and second edges of the elongated member.

7. The instrument of claim 6, wherein the wing and recess are located adjacent to the first end of the elongated member.

8. The instrument of claim 6, wherein the elongated member includes a curved region located between the first end of the elongated member and the wing.

9. A method of distracting first and second adjacent vertebral elements, the method comprising:
    a) providing a surgical instrument having;
        (i) an elongated member having a first end and a second end, and a first edge and a second edge, the first end defining a curved region, wherein the curved region of the elongated member has a convex curvature relative to the plane defined by the first and second edges of the elongated member;
        (ii) a handle extending from the elongated member, the handle being positioned adjacent to the second end of the elongated member; and
        (iii) a wing extending outward from the elongated member, the wing being positioned between the curved region and the handle;
    b) inserting the the curved region in a first orientation between the first and second vertebral elements;
    c) positioning the wing adjacent a nerve root; and
    d) rotating the instrument to simultaneously retract a nerve root and distract the first and second vertebral elements a distance.

10. The method of claim 9, wherein the distance of distraction is determined by a width of the elongated blade member.

11. The method of claim 9, wherein the instrument is rotated approximately 90 degrees.

* * * * *

UNITED STATES PATENT AND TRADEMARK OFFICE
CERTIFICATE OF CORRECTION

PATENT NO.         : 7,108,698 B2                                             Page 1 of 2
APPLICATION NO.    : 10/756040
DATED              : September 19, 2006
INVENTOR(S)        : Daniel S. Robbins et al.

It is certified that error appears in the above-identified patent and that said Letters Patent is hereby corrected as shown below:

IN THE SPECIFICATION:

Column 1, line 60, change "relates to a distracting" to --relates to distracting--.

Column 2, line 16, change "according to the principals" to --according to the principles--.

Column 2, line 47, change "in accordance with the principals" to --in accordance with the principles--.

Column 2, line 52, change "can be use to rotate" to --can be used to rotate--.

Column 3, line 1, change "In the illustrated," to --In the illustrated embodiment,--.

Column 4, line 59, change "nerve root out 80 of the way" to --nerve root 80 out of the way--.

Column 5, line 29, change "boring tools can inserted into" to --boring tools can be inserted into--.

Column 5, line 47, change "surgical tool 10 may simple be inserted" to --surgical tool 10 may simply be inserted--.

IN THE CLAIMS:

Column 6, line 31, change "first end and the handle" to --first end and the handle;--.

Column 6, line 41, change "providing a surgical instrument having;" to --providing a surgical instrument having:--.

UNITED STATES PATENT AND TRADEMARK OFFICE
CERTIFICATE OF CORRECTION

PATENT NO.        : 7,108,698 B2
APPLICATION NO. : 10/756040
DATED             : September 19, 2006
INVENTOR(S)       : Daniel S. Robbins et al.

It is certified that error appears in the above-identified patent and that said Letters Patent is hereby corrected as shown below:

Column 6, line 54, change "inserting the the curved" to --inserting the curved--.

Signed and Sealed this

Second Day of January, 2007

JON W. DUDAS
*Director of the United States Patent and Trademark Office*